US 11,234,700 B2

(12) United States Patent
Ragosta et al.

(10) Patent No.: US 11,234,700 B2
(45) Date of Patent: Feb. 1, 2022

(54) WRIST ARCHITECTURE

(71) Applicant: Intuitive Surgical Operations, Inc., Sunnyvale, CA (US)

(72) Inventors: Nicholas Ragosta, Sunnyvale, CA (US); Matthew A. Wixey, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 279 days.

(21) Appl. No.: 16/331,672

(22) PCT Filed: Sep. 8, 2017

(86) PCT No.: PCT/US2017/050754
§ 371 (c)(1),
(2) Date: Mar. 8, 2019

(87) PCT Pub. No.: WO2018/049211
PCT Pub. Date: Mar. 15, 2018

(65) Prior Publication Data
US 2019/0239877 A1  Aug. 8, 2019

Related U.S. Application Data

(60) Provisional application No. 62/385,621, filed on Sep. 9, 2016.

(51) Int. Cl.
*A61B 17/072* (2006.01)
*A61B 34/00* (2016.01)
(Continued)

(52) U.S. Cl.
CPC .. *A61B 17/07207* (2013.01); *A61B 17/00234* (2013.01); *A61B 34/30* (2016.02);
(Continued)

(58) Field of Classification Search
None
See application file for complete search history.

(56) References Cited

U.S. PATENT DOCUMENTS 9,161,771 B2    10/2015  Steger
2007/0250113 A1*  10/2007  Hegeman ....... A61B 17/320016
                                            606/207
(Continued)

FOREIGN PATENT DOCUMENTS

CN    101106945 A    1/2008
CN    102046101 A    5/2011
(Continued)

OTHER PUBLICATIONS

Office Action dated Dec. 29, 2020 for Chinese Application No. 20178054693 filed Sep. 8, 2017, 43 pages.
(Continued)

*Primary Examiner* — Anna K Kinsaul
*Assistant Examiner* — Chinyere J Rushing-Tucker
(74) *Attorney, Agent, or Firm* — Jones Robb, PLLC

(57) ABSTRACT

A surgical device includes an elongated shaft, an end effector, and a wrist assembly. The wrist assembly includes a first outer link, a first inner link, and a second outer link. The first outer link is connected to the shaft and includes first gear teeth. The first inner link is pivotally coupled with the first outer link. The second outer link is pivotally coupled with the first inner link. The second outer link includes second gear teeth that interface with the first gear teeth and control orientation of the first inner link relative to the first outer link and the first outer link throughout a range of orientations of the wrist assembly.

19 Claims, 11 Drawing Sheets

(51) Int. Cl.
    *A61B 34/30*     (2016.01)
    *A61B 17/00*     (2006.01)
    *A61B 17/29*     (2006.01)

(52) U.S. Cl.
    CPC .... *A61B 34/71* (2016.02); *A61B 2017/00314* (2013.01); *A61B 2017/00327* (2013.01); *A61B 2017/07285* (2013.01); *A61B 2017/2927* (2013.01); *A61B 2034/305* (2016.02)

(56) References Cited

U.S. PATENT DOCUMENTS

| | | | |
|---|---|---|---|
| 2010/0041945 A1 | 2/2010 | Isbell, Jr. | |
| 2010/0331857 A1* | 12/2010 | Doyle | A61B 34/30 606/130 |
| 2011/0152879 A1* | 6/2011 | Williams | A61B 34/71 606/130 |
| 2011/0152922 A1 | 6/2011 | Jeong | |
| 2013/0126586 A1* | 5/2013 | Zhang | A61B 17/07207 227/176.1 |
| 2014/0005653 A1* | 1/2014 | Shelton, IV | A61B 34/70 606/33 |
| 2014/0214049 A1* | 7/2014 | Jeong | A61B 17/00234 606/130 |
| 2014/0257331 A1* | 9/2014 | Kim | A61B 34/37 606/130 |

FOREIGN PATENT DOCUMENTS

| | | |
|---|---|---|
| CN | 102123672 A | 7/2011 |
| CN | 102440813 A | 5/2012 |
| CN | 104414737 A | 3/2015 |
| EP | 1997440 A2 | 12/2008 |
| EP | 1955659 B1 | 3/2011 |
| EP | 2371299 A1 | 10/2011 |
| EP | 2659854 A2 | 11/2013 |
| WO | WO-03001986 A2 | 1/2003 |
| WO | WO-2010019001 A2 | 2/2010 |
| WO | WO-2013162206 A1 | 10/2013 |
| WO | WO-2015127250 A1 | 8/2015 |
| WO | WO-2018049211 A1 | 3/2018 |

OTHER PUBLICATIONS

Extended European Search Report for Application No. EP17849645.1 dated Mar. 10, 2020, 8 pages.

International Search Report and Written Opinion for Application No. PCT/US2017/050754, dated Dec. 15, 2017, 18 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

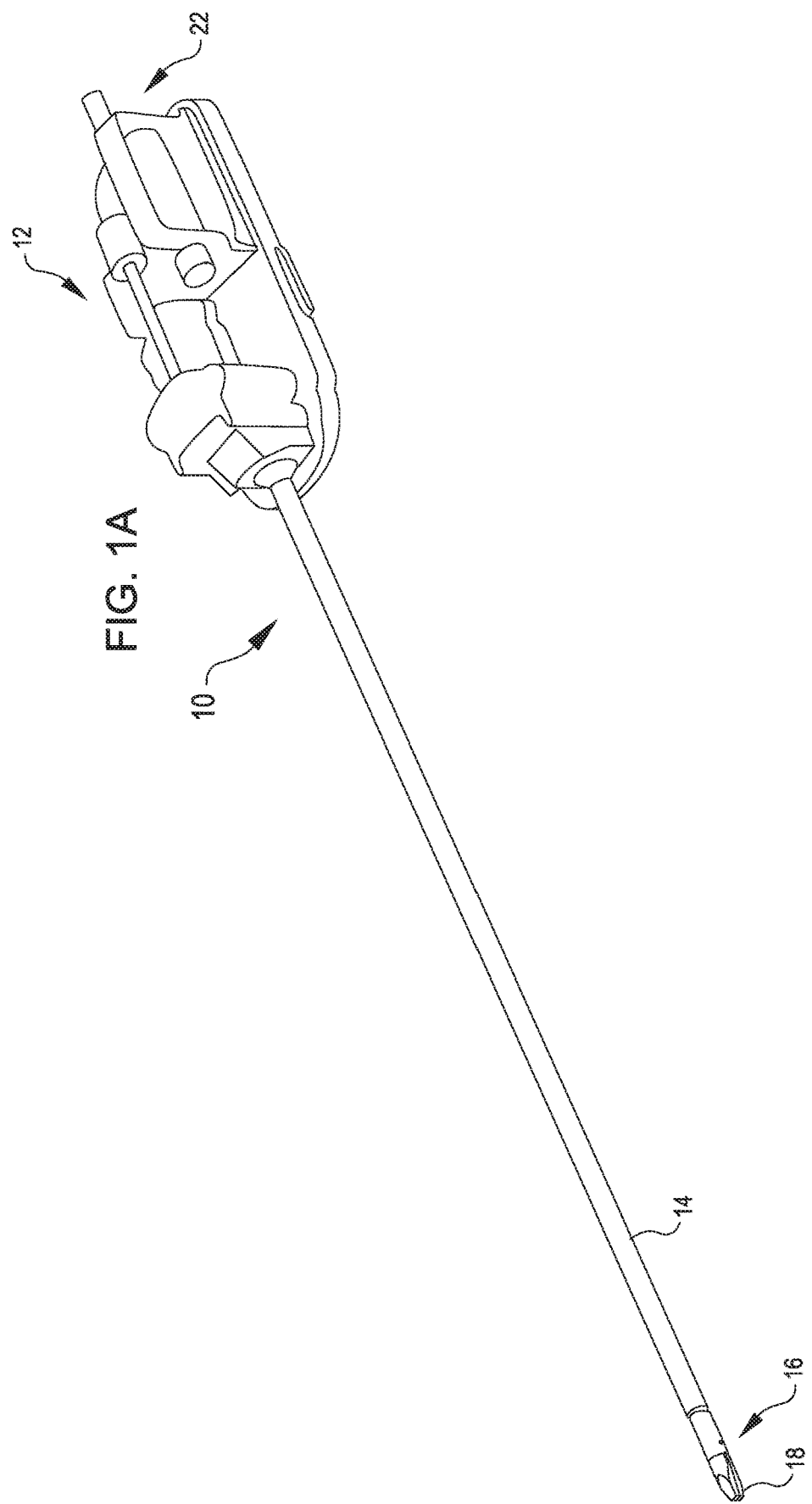

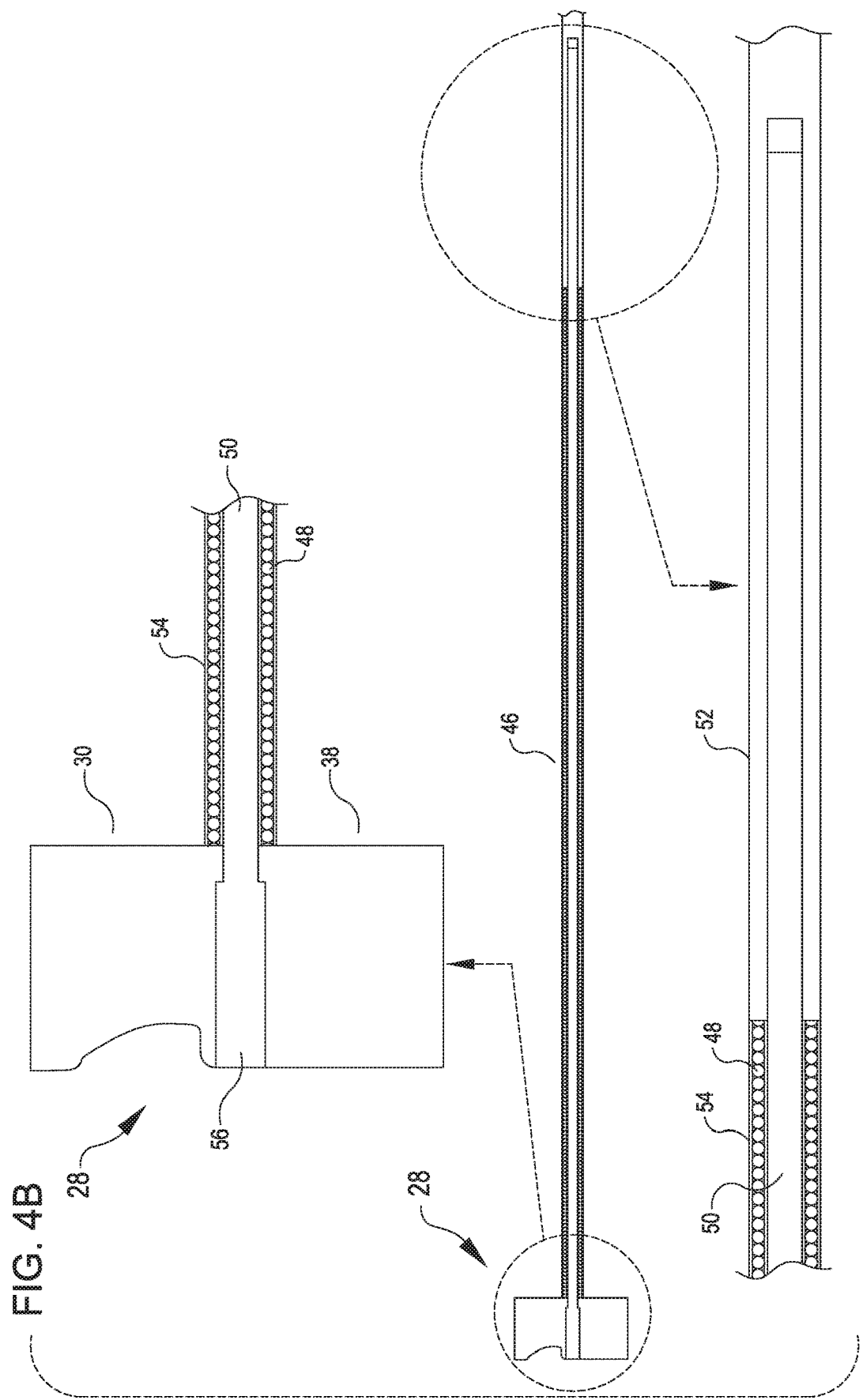

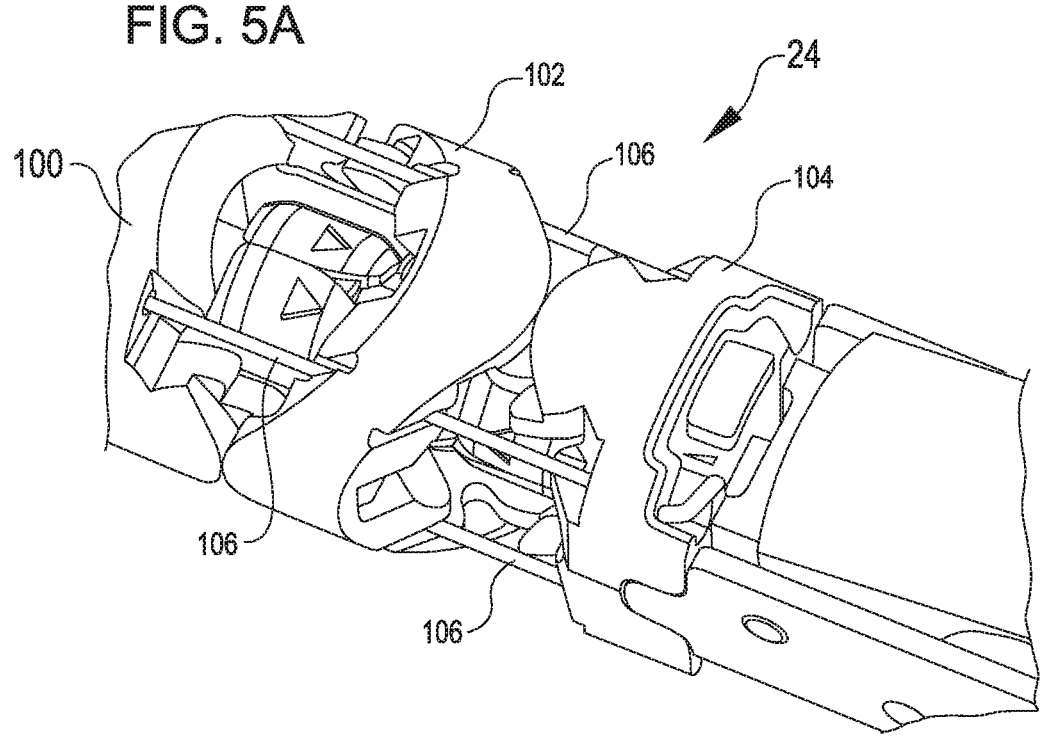

WRIST ARCHITECTURE

CROSS REFERENCE TO RELATED APPLICATION DATA

The present application is a U.S. National Stage Application of PCT/US2017/050754 filed Sep. 8, 2017; claims the benefit of U.S. Provisional Appln. No. 62/385,621 filed Sep. 9, 2016; the full disclosures which are incorporated herein by reference in their entirety for all purposes.

BACKGROUND

Minimally invasive surgical techniques are aimed at reducing the amount of extraneous tissue that is damaged during diagnostic or surgical procedures, thereby reducing patient recovery time, discomfort, and deleterious side effects. As a consequence, the average length of a hospital stay for standard surgery may be shortened significantly using minimally invasive surgical techniques. Also, patient recovery times, patient discomfort, surgical side effects, and time away from work may also be reduced with minimally invasive surgery.

A common form of minimally invasive surgery is endoscopy, and a common form of endoscopy is laparoscopy, which is minimally invasive inspection and/or surgery inside the abdominal cavity. Reloadable stapling devices can be used in conjunction with these surgeries. Telesurgically controlled stapling devices can include servo controlled wrist joints that yaw and pitch at relatively extreme angles (e.g., up to and over 90 degrees). Such joints can place a large amount of strain on actuation components that must translate through the wrist at such angles. Accordingly, current actuation devices are often limited by the ability of actuation components to function under extreme angles.

BRIEF SUMMARY

Embodiments disclosed herein relate to surgical devices having wrists that can yaw and pitch at relatively large angles. Such wrists can have a yaw axis spatially separated from a pitch axis, with both such axes being perpendicular to one another as well as a longitudinal axis that defines the extension of an arm or shaft of a telesurgically controlled device. In some cases, the yaw and pitch angles can be up to 45, 60, or 90 degrees.

Such pitch and yaw angles require an extremely flexible actuation mechanism for opening and closing jaws of the surgical device and optionally actuating other implements such as cutting and/or stapling devices. In some embodiments, an actuation mechanism can include a pushing component. The pushing component can be adapted to be highly compressible under extreme angles, while being extremely flexible. The pushing component may not however, be well suited to tensile forces. Accordingly a separate pulling component can be used to apply tensile force for proximal movement and actuation of the surgical device. In a similar manner, the pulling component may not be well suited for compressive forces. However, the combination of the pushing and pulling component into one integrated device can be effectively used for both compressive and tensile force application (i.e., pushing and pulling) to actuate components of an end effector of a surgical device.

The pushing component and the pulling component can be integrated along a shared axis with the pushing component being concentrically arranged about the pulling component. In some embodiments, the pushing component includes a coiled spring and the pulling component includes a braided cable. Alternatively the pulling component can be concentrically arranged about the pushing component.

To enable a high degree of wrist flexibility, the wrist assembly can be constructed from outer links that define yaw and pitch geometry for the wrist assembly. The outer links can house a flexible portion of the actuation mechanism. However, compression of the actuation mechanism within a wrist can cause buckling and decrease efficiency of force transmission. To help mitigate such issues, inner links can be provided that connect the outer links to one another. The inner links can define a passage that constrains and limits lateral movement of the actuation mechanism, and thus mitigate buckling.

Thus, in one aspect, an apparatus includes an elongated shaft, an end effector, and a wrist assembly. The elongated shaft extends along a first axis. The end effector includes an upper jaw and a lower jaw. The wrist assembly moveably connects the end effector to the elongated shaft. The wrist assembly includes a first outer link, a first inner link, and a second outer link. The first outer link is connected to the elongated shaft and movably coupled to the second outer link by the first inner link. The first outer link, the first inner link, and the second outer link define a proximal joint. A medial surface of the first outer link and a medial surface of the second outer link define a lumen in which the first inner link is disposed. The medial surface of the first outer link defines at least a first recess and the medial surface of the second outer link defines at least a second recess. A radial surface of the first inner link includes at least a first protrusion and a second protrusion. The first protrusion of the first inner link engages the first recess. The second protrusion of the inner link engages the second recess.

In some embodiments of the apparatus, the wrist assembly is operable to reorient to the end effector relative to the elongated shaft about an axis that is perpendicular to the first axis. For example, in some embodiments of the apparatus, the proximal joint extends along a second axis that is perpendicular to the first axis.

In some embodiments of the apparatus, the wrist assembly is operable to reorient to the end effector relative to the elongated shaft about each of two axes that are perpendicular to the first axis. For example, the wrist assembly can further include a second inner link and a third outer link. The third outer link is connected to the end effector and moveably coupled to the second outer link by the second inner link. The third outer link, the second inner link, and the second outer link define a distal joint. The wrist assembly can be configured to yaw and pitch at the proximal and distal joints, respectively. In some embodiments of the apparatus, each of the first inner link and the second inner link includes first and second clevis protruding journals.

In some embodiments of the apparatus, the wrist assembly has an interior passage through which an actuation component extends. For example, some embodiments of the apparatus include an elongated drive member drivingly coupled with the end effector and extending through an interior passage defined by the first inner link. In some embodiments of the apparatus, the elongated drive member is operable to apply a distally directed force to the end effector. In some embodiments, the interior passage is closely formed about the elongated drive member to prevent the elongated drive member from buckling while applying the distally directed force to the end effector. In some embodiments, the wrist assembly includes an inner sheath within the interior passage through which the elongated drive member extends.

In some embodiments of the apparatus, the first outer link and the second outer link interface so as to control relative orientation between the first outer link, the first inner link, and the second outer link during articulation of the wrist assembly. For example, in some embodiments, the first outer link and the second outer link include intermeshing gear teeth that control relative orientation between the first outer link, the first inner link, and the second outer link through a range of orientations between the second outer link and the first outer link. In some embodiments, the first inner link is passively constrained by the first outer link and the second outer link.

In another aspect, an apparatus includes an elongated arm, and end effector, an elongated drive member, and a wrist assembly. The elongated arm extends along a first axis. The end effector includes an upper jaw and a lower jaw. The elongated drive member extends from the elongated arm and is drivingly coupled with the end effector for actuation of the end effector. The wrist assembly moveably connects the elongated arm to the end effector. The wrist assembly includes a plurality of outer links and a plurality of inner links. The wrist assembly is operable to yaw and pitch the end effector relative to the elongated arm. The inner links define an inner passage between the elongated arm and the end effector through which the elongated drive member extends.

In some embodiments of the apparatus, the wrist assembly is operable to reorient to the end effector relative to the elongated shaft about an axis that is perpendicular to the first axis. For example, in some embodiments of the apparatus, the wrist assembly includes a proximal joint that extends along a second axis perpendicular to the first axis.

In some embodiments of the apparatus, the wrist assembly is operable to reorient to the end effector relative to the elongated shaft about each of two axes that are perpendicular to the first axis. For example, the wrist assembly can further include a distal joint that extends along a third axis perpendicular to the first axis and the second axis. In some embodiments, the wrist assembly is configured to yaw at the proximal joint and pitch at the distal joint. In some embodiments, each of the inner links comprises first and second protruding journals.

In some embodiments of the apparatus, the wrist assembly has an interior passage through which an actuation component extends. For example, some embodiments of the apparatus, the interior passage is closely formed about the elongated drive member to prevent the elongated drive member from buckling under compression. In some embodiments, the wrist assembly includes an inner sheath within the interior passage and through which the elongated drive member extends.

In some embodiments of the apparatus, the outer links interface so as to control relative orientation between the outer links and the inner links. For example, in some embodiments, the outer links include intermeshing gear teeth that control relative orientation between the outer links and the inner links through a range of orientations between the outer links. In some embodiments, the inner links are passively constrained by the outer links.

In some embodiments, the wrist assembly is actuated via tension members. For example, in some embodiments, the apparatus includes cable portions that extend through portions of the outer links and are articulated to articulate the wrist assembly.

In another aspect, a surgical device includes an elongated shaft, an end effector, and a wrist assembly. The elongated shaft extends along a first axis. The end effector includes an upper jaw and a lower jaw. The wrist assembly moveably connects the end effector to the elongated shaft. The wrist assembly includes a first outer link, a first inner link, and a second outer link. The first outer link is connected to the elongated shaft and includes first gear teeth. The first inner link is pivotally coupled with the first outer link to rotate relative to the first outer link around a second axis oriented perpendicular to the first axis. The second outer link is pivotally coupled with the first inner link to rotate relative to the first inner link around a third axis parallel to the second axis and offset from the second axis. The second outer link includes second gear teeth that interface with the first gear teeth and control orientation of the first inner link relative to the first outer link and the first outer link throughout a range of orientations of the second outer link relative to the first outer link.

The first inner link can be pivotally coupled with the first outer link and the second outer link using any suitable pivot connection. For example, in some embodiments of the surgical device: the first inner link includes a first pair of protruding journals aligned with the second axis and a second pair of protruding journals aligned with the third axis, the first outer link comprises a pair of first outer link journal bearings interfacing with the first pair of protruding journals, and the second outer link comprises a pair of second outer link journal bearings interfacing with the second pair of protruding journals.

The first inner link, the first outer link, or the second outer link can have a multiple-piece construction to facilitate assembly of the wrist assembly. For example, in some embodiments of the surgical device, the first inner link has a multiple-piece construction comprising a first inner link first portion and a first inner link second portion. In some embodiments of the surgical device, the first inner link first portion and the first inner link second portion are configured to be interfaced with one of the first outer link and the second outer link via rotation of each of the first inner link first portion and the first inner link second portion relative to the one of the first outer link and the second outer link. In some embodiments of the surgical device, the other of the one of the first outer link and the second outer link has a multiple-piece construction adapted to accommodate assembly to the first inner link after the first inner link is assembled with the one of the first outer link and the second outer link.

In some embodiments of the surgical device, the wrist assembly forms an aperture through which an actuation assembly extends. For example, in some embodiments, the first inner link forms the aperture and the surgical device includes an elongated drive member that extends through the aperture and is drivingly coupled with the end effector to actuate a mechanism of the end effector.

In some embodiments of the surgical device, the wrist assembly is cable driven and configured to react both proximally-directed loads and distally-directed loads applied to the end effector without relying on cable tension to react the distally-directed loads to keep the wrist assembly components from separating. For example, in some embodiments, the surgical device includes cable portions drivingly coupled with the wrist assembly and articulated to articulate the wrist assembly and the first inner link is configured to react both tension and compression loads applied to the end effector by the drive member back to the first outer link so as to keep the second outer link interfaced with the first outer link even in the absence of any of the cable portions being under tension.

In some embodiments of the surgical device, the wrist assembly is operable to reorient to the end effector relative to the elongated shaft about each of two axes that are perpendicular to the first axis. For example, the wrist assembly can further include a second inner link and a third outer link. The second inner link can be pivotally coupled with the second outer link to rotate relative to the second outer link around a fourth axis oriented perpendicular to the first axis and to the third axis. The third outer link can be pivotally coupled with the second inner link to rotate relative to the second inner link around a fifth axis parallel to the fourth axis and offset from the fourth axis. The third outer link can include gear teeth that interface with gear teeth of the second outer link and control orientation of the second inner link relative to the third outer link and the second outer link throughout a range of orientations of the third outer link relative to the second outer link.

The second inner link can be pivotally coupled with the second outer link and the third outer link using any suitable pivot connection. For example, in some embodiments of the surgical device: the second inner link includes a first pair of protruding journals aligned with the fourth axis and a second pair of protruding journals aligned with the fifth axis, the second outer link includes a pair of second outer link journal bearings interfacing with the first pair of protruding journals of the second inner link; and the third outer link includes a pair of third outer link journal bearings interfacing with the second pair of protruding journals of the second inner link.

The second inner link, the second outer link, or the third outer link can have a multiple-piece construction to facilitate assembly of the wrist assembly. For example, in some embodiments of the surgical device, the second inner link has a multiple-piece construction comprising a second inner link first portion and a second inner link second portion. In some embodiments, the second inner link first portion and the second inner link second portion are configured to be interfaced with one of the second outer link and the third outer link via rotation of each of the second inner link first portion and the second inner link second portion relative to the one of the second outer link and the third outer link. In some embodiments, the other of the one of the second outer link and the third outer link has a multiple-piece construction adapted to accommodate assembly to the second inner link after the second inner link is assembled with the one of the second outer link and the third outer link.

In some embodiments of the surgical device, the wrist assembly forms an aperture through which an actuation assembly extends. For example, in some embodiments, the second inner link forms a second inner link aperture. The surgical device can include an elongated drive member that extends through the second inner link aperture and is drivingly coupled with the end effector to actuate a mechanism of the end effector.

In some embodiments of the surgical device, the wrist assembly is cable driven and configured to react both proximally-directed loads and distally-directed loads applied to the end effector without relying on cable tension to react the distally-directed loads to keep the wrist assembly components from separating. For example, the surgical device can include cable portions drivingly coupled with the wrist assembly and articulated to articulate the wrist assembly. The first inner link and the second inner link can be configured to react both tension and compression loads applied to the end effector by the drive member back to the first outer link so as to keep the third outer link interfaced with the second outer link and the second outer link interfaced with the first outer link even in the absence of any of the cable portions being under tension.

BRIEF DESCRIPTION OF THE DRAWINGS

FIGS. 1A-1C show views of a surgical tool, according to many embodiments.

FIG. 4B shows a cross-sectional view of an actuation mechanism, according to many embodiments.

FIG. 5A shows a perspective view of a wrist assembly, according to many embodiments.

DETAILED DESCRIPTION

Figure 1B:
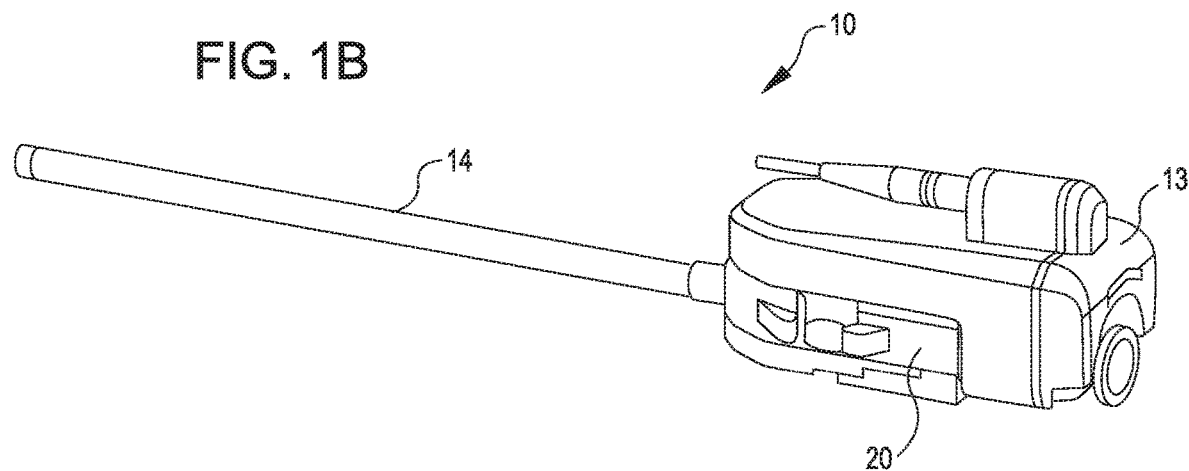
Figure 1C:
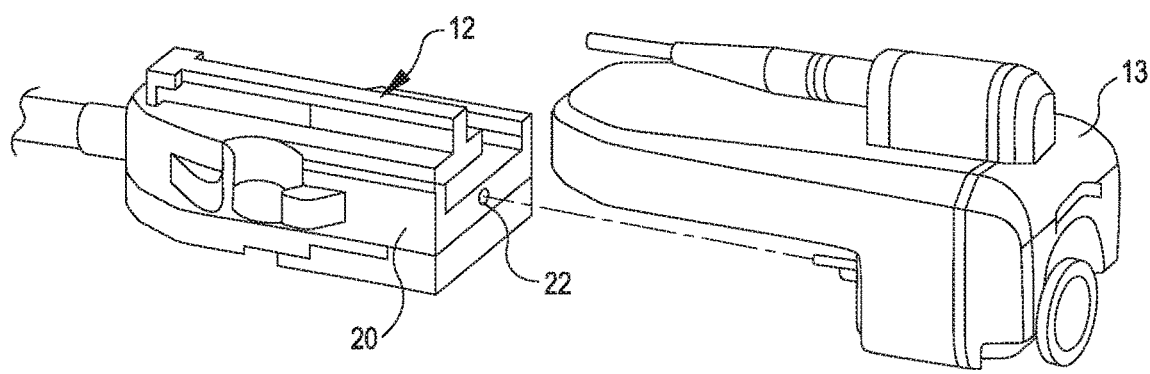

FIGS. 1A-1C show a surgical tool 10 that includes a proximal chassis 12, an instrument shaft 14, and a distal end effector 16 having an upper jaw 18 that can be articulated to grip a patient tissue. The proximal chassis 12 includes input couplers 22 that may interface with and be driven by corresponding output couplers of a telesurgical surgery system, such as the system disclosed within Pub. No. US 2014/0183244 A1, which is incorporated by reference herein. The input couplers 22 are drivingly coupled with one or more input members that are disposed within the instrument shaft 14. The input members are drivingly coupled with the end effector 16. As shown at FIGS. 1B and 1C, input couplers 22 of the proximal chassis 12 can be adapted to mate with various types of motor packs 13, such as stapler specific motor packs disclosed at U.S. Pat. No. 8,912,746, or the universal motor packs disclosed at U.S. Pat. No. 8,529,582, which are incorporated by reference herein.

Figure 2A:
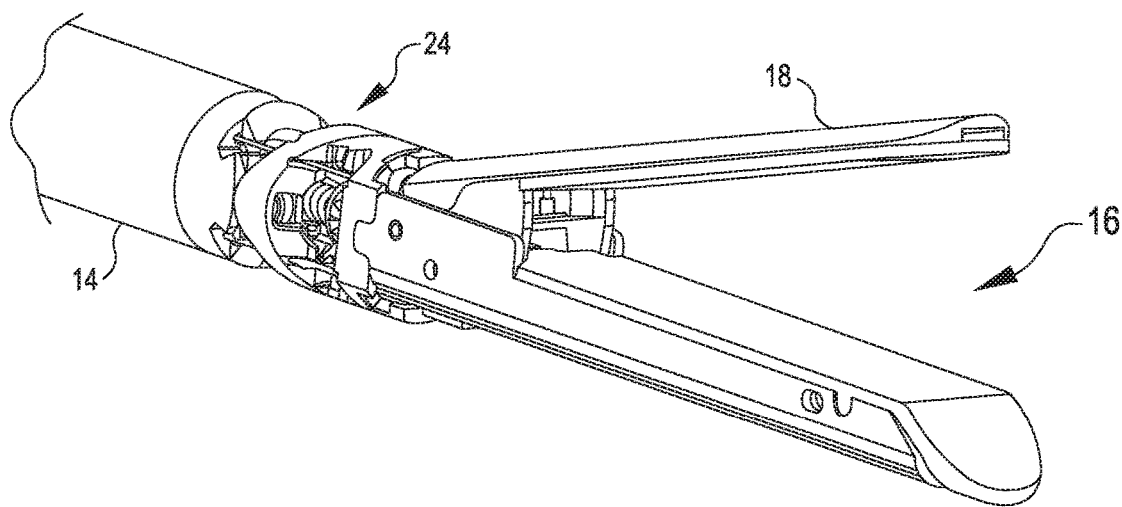
FIGS. 2A, 2B, and 2C shows a perspective, side, and bottom views of a surgical tool, according to many embodiments.
Figure 2B:
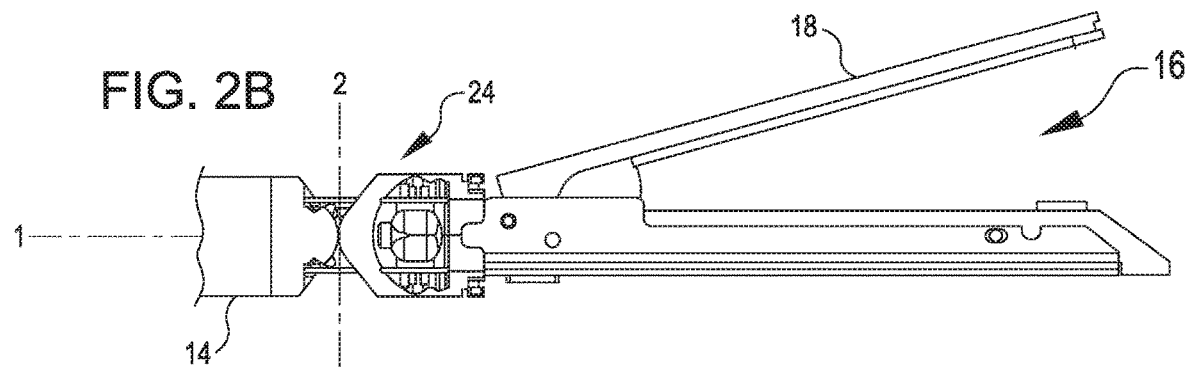
Figure 2C:
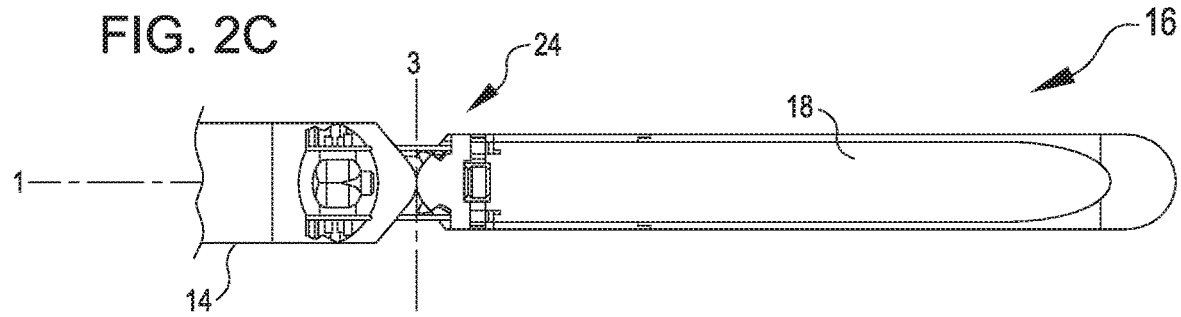

FIGS. 2A-2C show perspective, side, and top views of a distal end of the surgical tool 10 including the end effector 16. End effector 16 is moveably connected to the instrument shaft 14 by a wrist assembly 24. The wrist assembly 24 has at least two degree of freedom and provides for attachment of the end effector 16 to the elongated instrument shaft 14 for articulation of the end effector 16 about two orthogonal axes relative to the instrument shaft 14. The wrist assembly 24 is configured to yaw about axis 2-2, which is perpendicular to axis 1 that the instrument shaft 14 extends along. The wrist assembly 24 is also configured to pitch about axis 3, which is perpendicular to axis 1 and axis 2. As shown, the yaw axis 2 is proximal (farther from the end effector 16) to the pitch axis 3, however this is not a requirement and in some embodiments the yaw axis 2 is distal to the pitch axis 3.

Figure 3A:
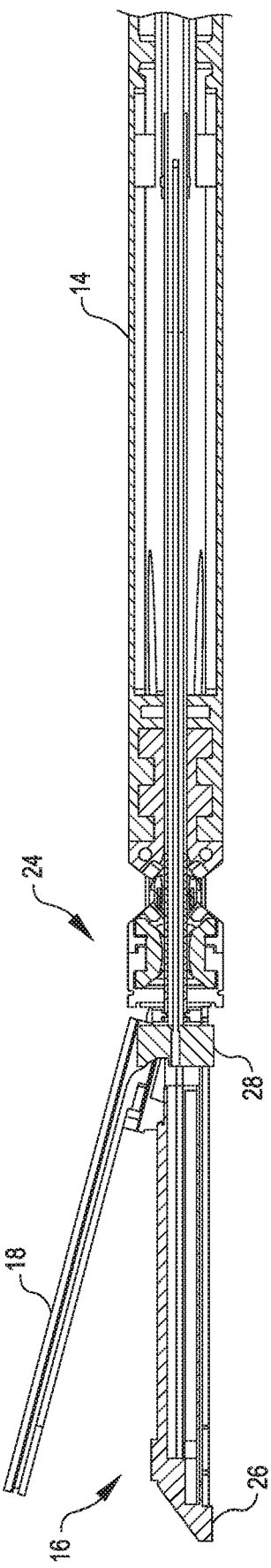
FIGS. 3A and 3B show cross-sectional views of a surgical tool, according to many embodiments.
Figure 3B:
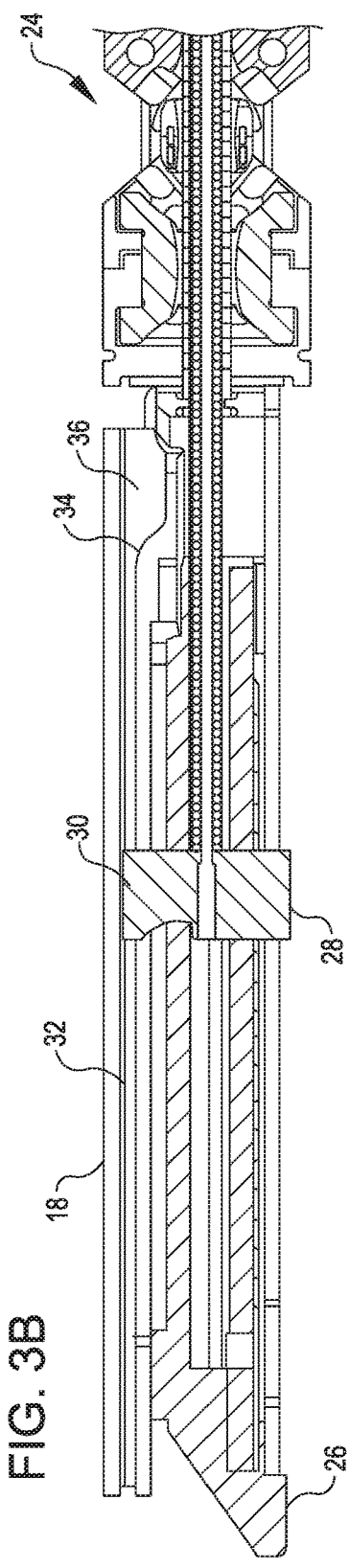

FIGS. 3A and 3B are a cross-sectional views showing details of end effector 16 that include the upper jaw 18 and a lower jaw 26. The lower jaw 26 can be configured to accommodate and support a removable or non-removable stapling cartridge. The upper jaw 18 is pivotally coupled with the lower jaw 26 to articulate relative to the lower jaw 26 to clamp tissue. A beam member 28 is driven from a proximal state shown at FIG. 3A to a distal state shown at FIG. 3B to actuate the upper jaw 18. Movement of the beam member 28 can serve to forcibly secure the upper jaw 18 over tissue with respect to the lower jaw 16. Optionally, the beam member 28 can also allow for cutting tissue and deploying staples from the cartridge into the cut tissue.

The beam member 28 includes an upper beam portion 30 that is configured to slide within a rail feature 32 of the upper jaw 18. The rail feature 32 includes a ramp 34 for the upper beam portion 30 to engage from a proximal most garage area 36. The open position shown at FIG. 3A can be maintained by a resilient device, such as a spring, or opened and closed by a secondary mechanism (not shown). Partial closure of the upper jaw 18 can be affected by distal movement of the upper beam portion 30 onto the ramp 34. Complete closure of the upper jaw 18 is achieved when the upper beam portion 30 is moved distally past the ramp 34 and onto the rail feature 32. Proximal movement of the upper beam portion 30 off of the ramp 34 removes the closure force applied by the beam member. A resilient device or secondary mechanism can then cause a closed or partially closed upper jaw 18 to open. Thus, back and forth movement of the upper beam portion 30 along the ramp 34 can toggle the end effector 16 open and closed.

The beam member 28 also includes a lower beam portion 38 that configured to slide within a rail feature 32 of the lower jaw 18. The lower beam portion 38 can actuate a sled (such as disclosed in Pub. No. US 2014/0183244 A1) configured for ejecting staples out the lower jaw 26 during distal movement of the beam member 28. Alternatively, the lower beam portion 30 can be integrated with such a sled.

Figure 4A:
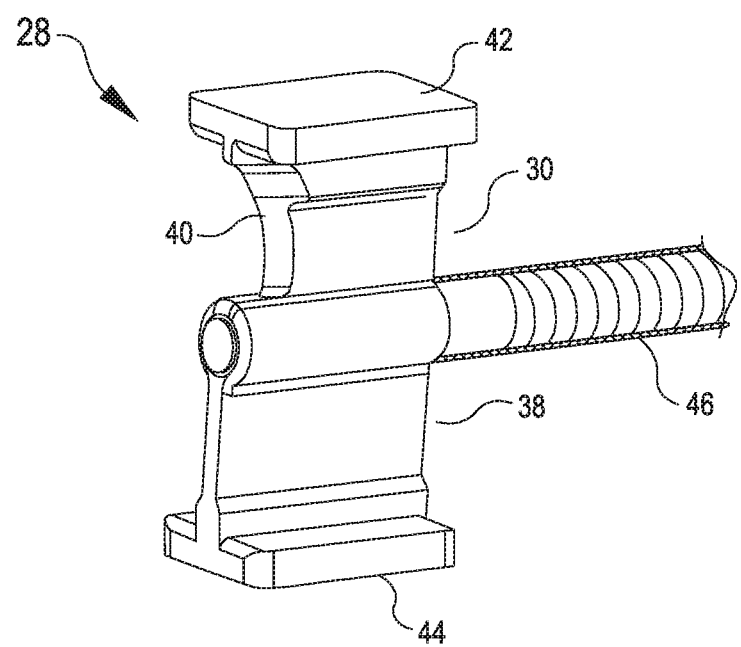
FIG. 4A shows a perspective view of an actuation mechanism, according to many embodiments.

FIG. 4A shows a perspective view of the beam member 28. Here, the upper beam portion 30 includes an integrated cutting member 40 that is configured to cut tissue. However, in other embodiments a tissue cutting device can be separate from the beam member 28 or implemented into the beam member 28 in a different manner. The upper beam portion 30 includes an upper flange 42, which transversely extends from the integrated cutting member 40. The gliding portion 42 is configured to directly interface with the rail feature 32 and ramp 34. In a similar manner a lower flange 44 is provided to slide with a rail feature of the lower jaw 26. An elongated drive member 46 is attached to the beam member 28 for providing distal and proximal movement to the drive member 46.

FIG. 4B shows a cross-sectional view of the beam member 28 and drive member 46. The drive member 46 includes a pushing member 48 and a pulling member 50. The pushing member 48 is configured as a close-coiled spring and is adapted for translating axial force applied by a drive rod 52. The pushing member 48 can be externally constrained by a sheath 54, which can be constructed from a lubricous polymer material such as PTFE. The coiled design of the pushing member 48 allows compressive force to be translated effectively to the beam member 28 to push the beam member 28 in the distal direction. The pushing member 48 can be constructed from a coiled wire in the conventional manner or be spirally cut from a tube. In some cases, the compressive elements (e.g., coils) of the pushing member will separate under tension, and thus in such cases the pushing member can only be effective for transfer of compressive forces.

The pulling member 50 can be constructed from a braided cable or other flexible rod and retained within the beam member 28 by crimp portion 56. In some cases, the pulling member may be relatively ineffective for transfer of pushing forces as it can have the tendency to collapse or buckle on itself, and thus in such cases the pulling member can only be effective for transfer of tensile forces. The pulling member 50 is also adapted for translating axial force applied by a drive rod 52. The drive rod 52 is located within the instrument shaft 14 and is drivingly coupled to one or more of the input couplers 22 shown at FIG. 1. The pulling member 50 allows tensile force to be translated effectively from the drive rod 52 to the beam member 28, to pull the beam member 28 in the proximal direction. The pushing member 48 and pulling member 50 operate in a complementary manner to provide distal and proximal motion to the beam member 28 by segregating tensile forces to the pulling member 50 and the compressive forces to the pushing member 48. This enables a very flexible and compact design for the drive member 46, characteristics that enable the drive member 46 to translate within the wrist 24, which can be disposed at torturous yaw and pitch angles during operation.

Figure 4C:
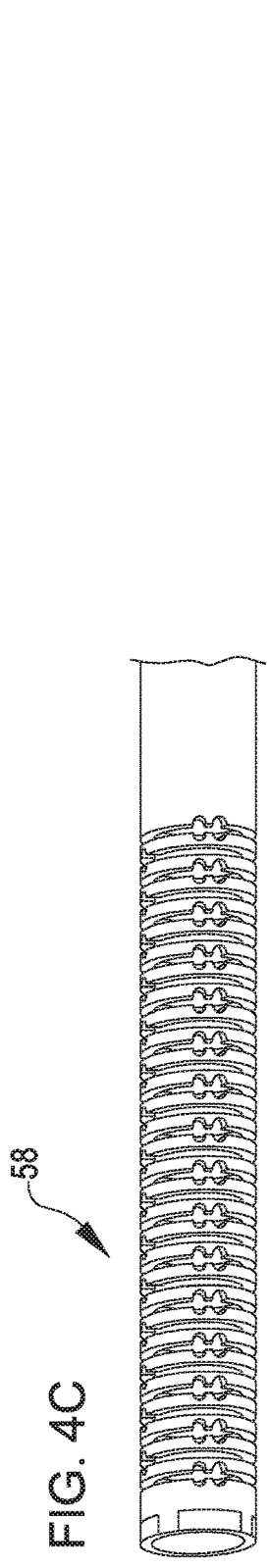
FIGS. 4C and 4D show perspective views of pushing members, according to many embodiments.
Figure 4D:
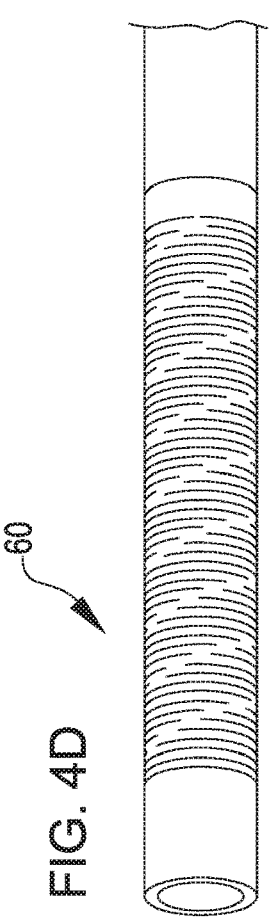

The pushing member is not limited to a close-coiled spring design as depicted at FIG. 4B. For example, a flexible pushing member 58 as shown at FIG. 4C can be formed from a solid tube by cutting a pattern into the solid tube to increase bending flexibility at the wrist without materially decreasing compressive stiffness. Here, the pushing member 58 is formed by laser cutting a pattern into a metal tube. The pattern here allows for flexibility where gaps are formed in the tube and axial stiffness where material is left in place. Another example of a flexible pushing member is depicted at FIG. 4D, which shows a pushing member 60 having a plurality of circumferential slits arranged in a spiraling pattern.

Figure 4E:
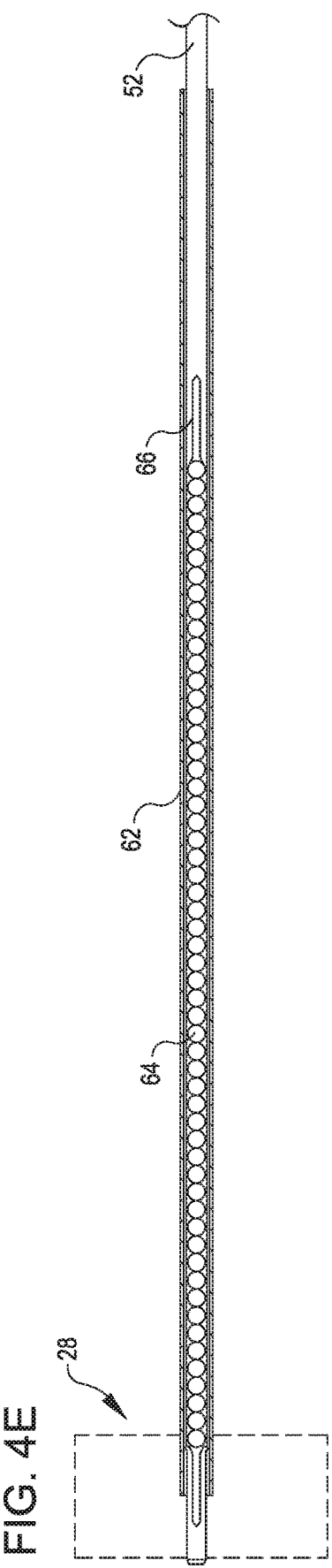
FIG. 4E shows a cross-sectional view of an actuation mechanism, according to many embodiments.

FIG. 4E shows an alternative configuration of a drive member 60. The configuration here is the opposite as what is depicted at FIG. 4B in which the pushing member 48 is concentrically surrounds the pulling member 50. Here, the drive member 60 includes a pulling member 62 configured as an braided sheath that encapsulates a pushing member 64. The pushing member 64 is configured as a plurality of spherical members (e.g., ball bearings) joined by a flexible rod 66. Both the pushing member 64 and pulling member 62 are actuated by the drive rod 52, which is drivingly coupled to one or more of the input couplers 22 shown at FIG. 1.

Figure 5B:
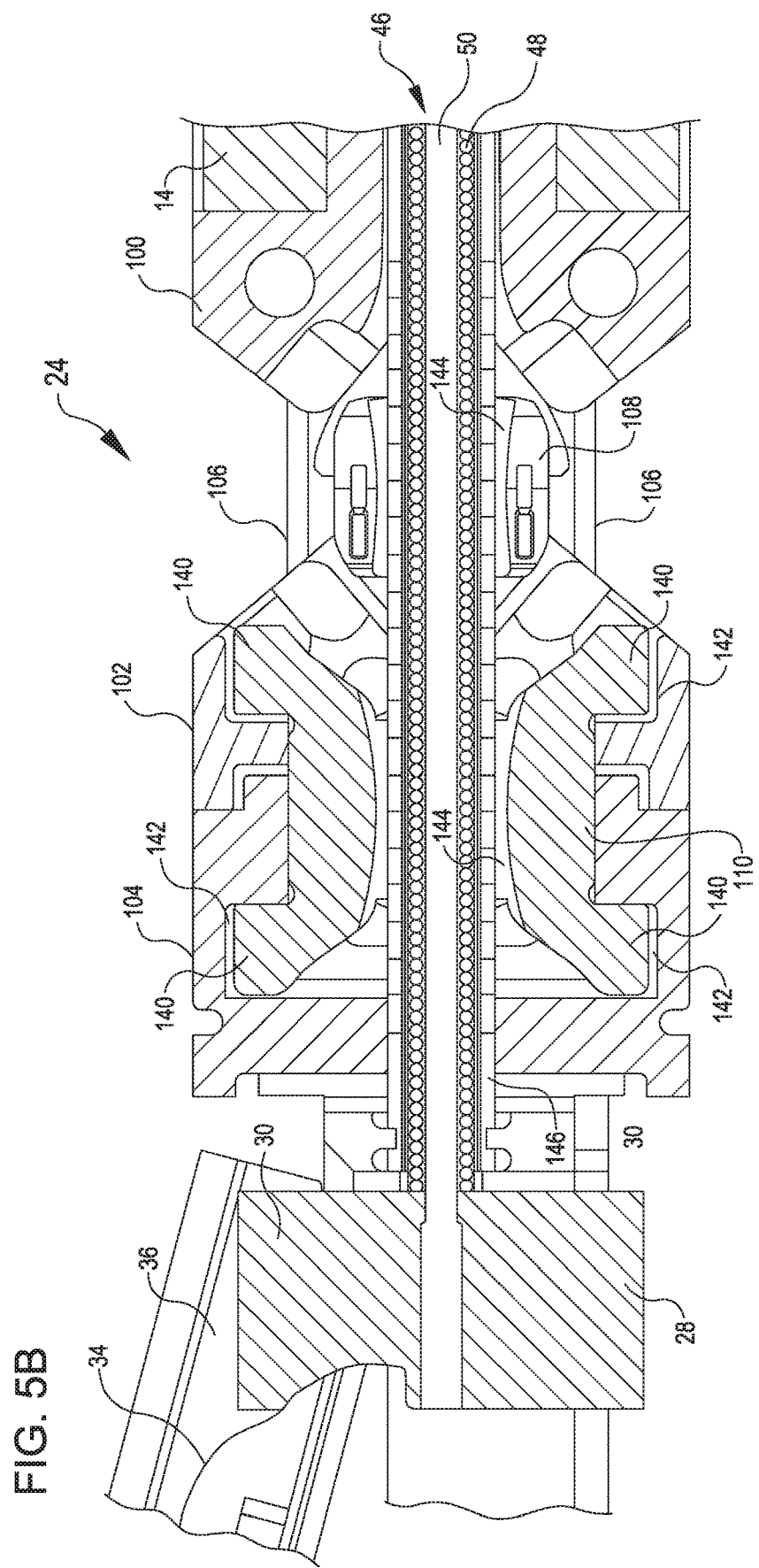
FIG. 5B shows a cross-sectional view of a wrist assembly, according to many embodiments.

FIGS. 5A and 5B show perspective and cross-sectional views of the wrist assembly 24. The wrist assembly 24 includes a proximal outer link 100, a middle outer link 102, and a distal outer link 104. These three links determine the kinematic pitch and yaw motion of the wrist assembly 24. As shown, the interface between the proximal outer link 100 and the middle outer link 102 determine yaw movement of the wrist assembly 24. The interface between the outer distal link 104 and the middle outer link 102 determine pitch movement of the wrist assembly 24. However, in an alternative wrist configuration, this relationship can be reversed such that the wrist assembly 24 pitches between the proximal outer link 100 and the middle outer link 102 and yaws between the distal outer link 100 and the middle outer link 102 (e.g., by rotating the end effector 16 relative to wrist assembly 24 by 90 degrees).

Cable portions 106 are drivingly coupled with the wrist assembly 24 and actuated to impart motion to the wrist assembly 24. In some embodiments, cable portions 106 can be individually secured to a portion of the distal outer link 104. In an functionally equivalent alternate embodiment, as shown at FIG. 5A, cable portions 106 are looped about a portion of the distal outer link 104 as shown. Looping cable portions 106 to the distal outer link 104 can be used to secure the cable portions 106 to the distal outer link 104. The cable portions 106 can be articulated to articulate the wrist assembly 24. Differential movement of the cable portions 106 can be used to actuate the wrist assembly 24 to pitch and yaw at various angles. The cable portions 106 can be drivingly coupled to one or more of the input couplers 22 shown at FIG. 1. The wrist assembly also includes proximal inner link 108 and distal inner link 110, which are discussed in detail below.

Figure 5C:
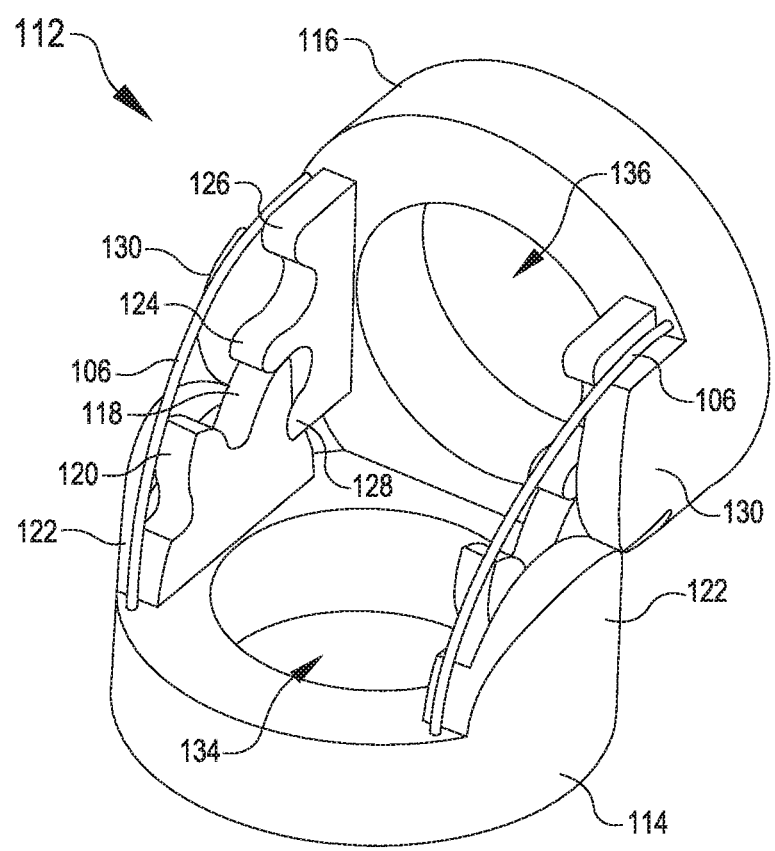
FIG. 5C shows a perspective view of an outer link assembly, according to many embodiments.

With attention to FIG. 5C, an exemplary embodiment of a joint 112 is shown that is representative of the interfaces between the outer links shown at FIGS. 5A and 5B. The joint 112 includes a first link 114 and a second link 116. First link 114 may include gear teeth 118, 120 and a bearing projection 122. The second link 116 includes gear teeth 124, 126, 128 and a bearing projection 130. According to an exemplary embodiment, projections 122, 130 of first and second links 114, 116 may include passages to permit cable portions 106 to pass through. Because bearing projections 122, 130 are located at an outboard location relative to central apertures 134, 136, cable portions 106 extending through passages adjacent to bearing projections 122, 130 also are located at an outboard location. This allows for routing of other mechanisms through the central apertures 134, 136. Actuation kinematics between the links 114, 116 are determined by the shape of the gear teeth 118, 120, 124, 126, 128, which engage and disengage during movement. The bearing projections 122, 130 included curved surfaces that can engage at suitable point throughout all angular motion to help reduce compressive strain to the gear teeth 118, 120, 124, 126, 128.

Due to the enhanced range of motion provided by joint 112, a wrist including joint 112 may provide a desired amount of motion, such as +/−90 degrees in a pitch or yaw direction, in a more efficient manner with fewer parts. In previous wrist structures in which each joint is limited to a maximum roll angle of about 45 degrees, several such joints in series are needed to achieve relatively large roll angle for the entire wrist mechanism. In the illustrated embodiment, a single joint 112 can provide up to a 90 degree angular deflection. As a result, manufacturing cost and complexity for a wrist that includes one or more joints 112 may be reduced while still achieving desired angular deflection. In addition, the gear teeth 118, 120, 124, 126, 128 included in links 114, 116 of joint 112 can provide enhanced timing to assist with accurately positioning links 114, 116, including, for example, returning links 114, 116 to a neutral position (e.g., zero angle roll alignment), and to enhance smoothness of the motion between links 114, 116, such as when links 114, 116 are reoriented relative to one another. According to an exemplary embodiment, a wrist may include a plurality of joints 112 to achieve higher ranges of motion (up to roll limit angles), such as, for example, wrists having a range of motion of up to +/−180 degrees in a pitch or yaw direction. Additional details of joint 112, and other joints usable with the embodiments disclosed herein, are disclosed in Int'l. Pub. No. WO 2015/127250, which is incorporated by reference herein.

As shown at FIG. 5B, the proximal and distal inner links 108, 110 are spatially separated along axis 1 and offset 90 degrees from one another. Hence, the proximal internal link 108 is only partially shown. Radial surfaces of the proximal and distal inner links 108, 110 include protrusions (e.g. configured as protruding journals 140). The protrusions interface with recesses (e.g. configured as journal bearings 142) at medial surfaces of the external links. In some embodiments, the protruding journals 140 and the journal bearings 142 set the distances between the outer links, but otherwise are passive and do not alter joint kinematics of the outer links which is determined by the geometry of the gear teeth 118, 120, 124, 126, 128. Each side of the proximal and distal inner links 108, 110 includes a pair of commonly aligned protruding journals 120 that interface with the journals bearings 142 for a total of four protruding journals 140 per inner link 108, 110. Each pair of protruding journals 140 is separated to provide an internal passage 144 for the drive member 46.

An additional internal sheath 146 can be used to further support the drive member 46. The drive member 46 slides axially within the internal sheath 146. The internal sheath 146 is fixed to a distal end portion of the wrist assembly 24 and is flexible to bend with movement of the wrist assembly 24 but does not move axially. The internal sheath 146 and internal passage 144 provided by the inner links 108, 110 serve to guide and constrain the drive member 46 during axial movement. Internal sheath 146 and inner passage 144 prevent the drive member from buckling under compressive loading (i.e. distal movement while cutting and stapling). Prior wrist designs, such as disclosed in the aforementioned Int'l. Pub. No. WO 2015/127250, rely on tensioned cables to maintain the outer links in position. Here, when the drive member 46 moves in a distal direction the resulting compressive force can be reacted by via the inner links 108, 110, thereby preventing potential stretching and resulting loss in tension in the cables 106. The protruding journals 140 of the inner links 108, 110 advantageously maintain the outer links in position when the drive member 46 moves in a distal direction, therefore maintaining the structure of the wrist assembly 24.

Figure 6A:
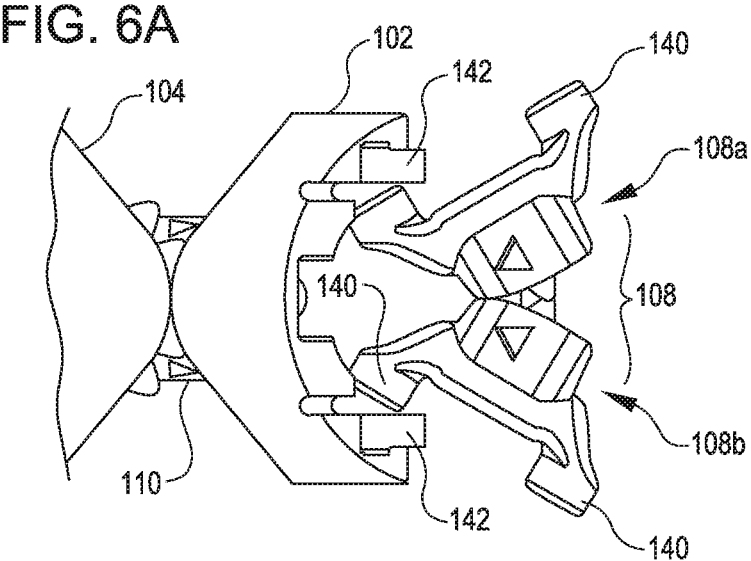
FIGS. 6A-6C show a method of assembling a wrist assembly, according to many embodiments.
Figure 6B:
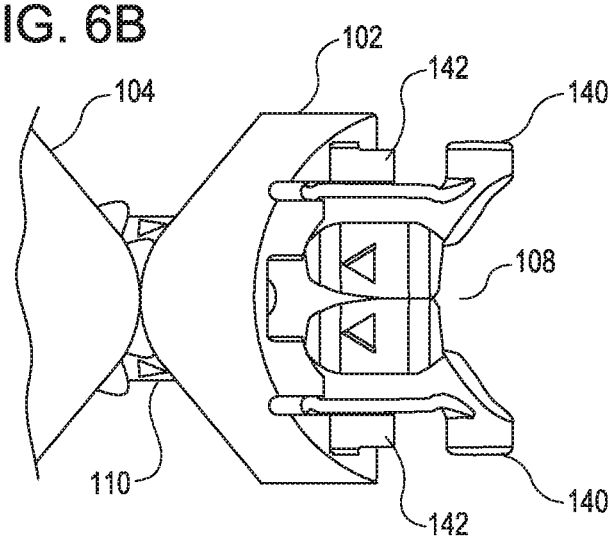
Figure 6C:
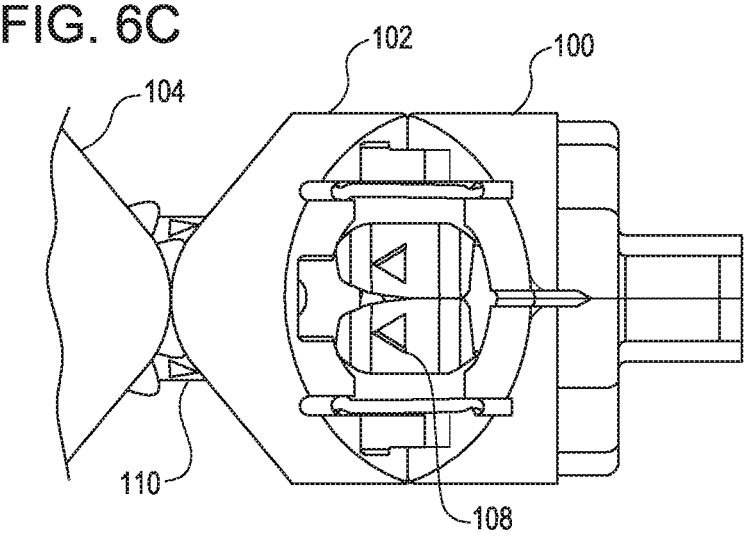

Each inner link 108, 110 can have a two-piece construction as depicted at FIGS. 6A through 6C, which also depict a technique for assembling the inner links to the outer links. At FIG. 6A first link portion 108a and second link portion 108b of the proximal inner link 108 are positioned to place protruding journals 140 into journal bearings 142 of the middle outer link 102. The first link portion 108a and second link portion 108b are inserted at angles such that gear teeth 148 of each portion intermesh to cause alignment of the portions into the formation shown at FIG. 6B. The gear teeth 148 are an assembly aid that eliminates the need for pins or other fasteners, and are not used for movement beyond assembly. However, in some embodiments, fasteners can be used in lieu of the gear teeth. After the link portions 108a, 108b are assembled into a complete inner proximal link 108, the proximal outer link 100 is assembled onto the remaining exposed protruding journals 140 into the formation shown at FIG. 6C. In one embodiment, as shown at FIG. 6C, proximal outer link 100 is also of two-piece construction.

Other variations are within the spirit of the present invention. The various aspects, embodiments, implementations or features of the described embodiments can be used separately or in any combination. Various aspects of the described embodiments associated with operation of telesurgical tools can be implemented by software, hardware or a combination of hardware and software. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A surgical device comprising:
    an elongated shaft extending along a first axis;
    an end effector comprising an upper jaw and a lower jaw; and
    a wrist assembly moveably connecting the end effector to the elongated shaft, the wrist assembly comprising:
        a first outer link connected to the elongated shaft and comprising first gear teeth;
        a first inner link pivotally coupled with the first outer link to rotate relative to the first outer link around a second axis oriented perpendicular to the first axis; and
        a second outer link pivotally coupled with the first inner link to rotate relative to the first inner link around a third axis parallel to the second axis and offset from the second axis, the second outer link comprising second gear teeth that interface with the first gear teeth and control orientation of the first inner link relative to the first outer link and the second outer link throughout a range of orientations of the second outer link relative to the first outer link.

2. The surgical device of claim 1, wherein:
    the first inner link comprises a first pair of protruding journals aligned with the second axis and a second pair of protruding journals aligned with the third axis;
    the first outer link comprises a pair of first outer link journal bearings interfacing with the first pair of protruding journals; and
    the second outer link comprises a pair of second outer link journal bearings interfacing with the second pair of protruding journals.

3. The surgical device of claim 1, wherein the first inner link has a multiple-piece construction comprising a first inner link first portion and a first inner link second portion.

4. The surgical device of claim 3, wherein the first inner link first portion and the first inner link second portion are configured to be interfaced with one of the first outer link and the second outer link via rotation of each of the first inner link first portion and the first inner link second portion relative to the one of the first outer link and the second outer link.

5. The surgical device of claim 4, wherein the other of the one of the first outer link and the second outer link has a multiple-piece construction adapted to accommodate assembly to the first inner link after the first inner link is assembled with the one of the first outer link and the second outer link.

6. The surgical device of claim 1, wherein the first inner link forms an aperture, the surgical device further comprising an elongated drive member that extends through the aperture and is drivingly coupled with the end effector to actuate a mechanism of the end effector.

7. The surgical device of claim 6, further comprising cable portions drivingly coupled with the wrist assembly and articulated to articulate the wrist assembly, and wherein the first inner link is configured to react both tension and compression loads applied to the end effector by the elongated drive member back to the first outer link so as to keep the second outer link interfaced with the first outer link even in the absence of any of the cable portions being under tension.

8. The surgical device of claim 1, wherein the wrist assembly further comprises:
    a second inner link pivotally coupled with the second outer link to rotate relative to the second outer link around a fourth axis oriented perpendicular to the first axis and to the third axis; and
    a third outer link pivotally coupled with the second inner link to rotate relative to the second inner link around a fifth axis parallel to the fourth axis and offset from the fourth axis, the third outer link comprising gear teeth that interface with gear teeth of the second outer link and control orientation of the second inner link relative to the third outer link and the second outer link throughout a range of orientations of the third outer link relative to the second outer link.

9. The surgical device of claim 8, wherein:
    the second inner link comprises a first pair of protruding journals aligned with the fourth axis and a second pair of protruding journals aligned with the fifth axis;
    the second outer link comprises a pair of second outer link journal bearings interfacing with the first pair of protruding journals of the second inner link; and
    the third outer link comprises a pair of third outer link journal bearings interfacing with the second pair of protruding journals of the second inner link.

10. The surgical device of claim 8, wherein the second inner link has a multiple-piece construction comprising a second inner link first portion and a second inner link second portion.

11. The surgical device of claim 10, wherein the second inner link first portion and the second inner link second portion are configured to be interfaced with one of the second outer link and the third outer link via rotation of each of the second inner link first portion and the second inner link second portion relative to the one of the second outer link and the third outer link.

12. The surgical device of claim 11, wherein the other of the one of the second outer link and the third outer link has a multiple-piece construction adapted to accommodate assembly to the second inner link after the second inner link is assembled with the one of the second outer link and the third outer link.

13. The surgical device of claim 8, wherein the second inner link forms a second inner link aperture, the surgical device further comprising an elongated drive member that extends through the second inner link aperture and is drivingly coupled with the end effector to actuate a mechanism of the end effector.

14. The surgical device of claim 13, further comprising cable portions drivingly coupled with the wrist assembly and articulated to articulate the wrist assembly, and wherein the first inner link and the second inner link are configured to react both tension and compression loads applied to the end effector by the elongated drive member back to the first outer link so as to keep the third outer link interfaced with the second outer link and the second outer link interfaced with the first outer link even in the absence of any of the cable portions being under tension.

15. An apparatus comprising:
   an elongated shaft extending along a shaft axis;
   an end effector comprising an upper jaw and a lower jaw; and
   a wrist assembly moveably connecting the end effector to the elongated shaft, the wrist assembly comprising:
      a first outer link, a first inner link, and a second outer link; the first outer link being connected to the elongated shaft and movably coupled to the second outer link by the first inner link; the first outer link, the first inner link, and the second outer link defining a proximal joint;
      wherein a medial surface of the first outer link and a medial surface of the second outer link define a lumen in which the first inner link is disposed;
      wherein the medial surface of the first outer link defines a pair of first recesses and the medial surface of the second outer link defines a pair of second recesses, wherein the pair of first recesses are aligned with a first axis about which the first inner link is constrained to rotate relative to the first outer link, wherein the pair of second recesses are aligned with a second axis about which the second outer link is constrained to rotate relative to the first inner link, and wherein the second axis is offset from and parallel with the first axis;
      wherein a radial surface of the first inner link includes a pair of first protrusions and a pair of second protrusions;
      wherein each protrusion of the first pair of protrusions engages a respective one of the recesses of the first pair of recesses; and
      wherein each protrusion of the second pair of protrusions engages a respective one of the recesses of the second pair of recesses.

16. The apparatus of claim 15, wherein each of the first axis and the second axis is perpendicular to the shaft axis.

17. The apparatus of claim 15, wherein the wrist assembly further comprises a second inner link and a third outer link, the third outer link being connected to the end effector and moveably coupled to the second outer link by the second inner link; the third outer link, the second inner link, and the second outer link defining a distal joint.

18. An apparatus comprising:
   a proximal chassis comprising a drive mechanism;
   an elongated arm coupled with the proximal chassis, wherein the elongated arm extends along a first axis and defines a shaft lumen;
   an end effector comprising an upper jaw and a lower jaw;
   an elongated drive member extending through the shaft lumen and drivingly coupling the drive mechanism with the end effector for actuation of the end effector; and
   a wrist comprising outer links and inner links, wherein the end effector is supported by the elongated arm via the outer links and the inner links, wherein each of the inner links is pivotally coupled with each of two of the outer links, wherein the wrist being operable to yaw and pitch the end effector relative to the elongated arm, and wherein the inner links define an inner passage between the elongated arm and the end effector through which the elongated drive member extends.

19. The apparatus of claim 18, wherein each of the outer links comprises gear teeth, and wherein the gear teeth of each of the outer links interface with the gear teeth of another of the outer links.

* * * * *